US00PP22135P2

(12) United States Plant Patent
Westhoff

(10) Patent No.: US PP22,135 P2
(45) Date of Patent: Sep. 6, 2011

(54) ***LOBELIA* PLANT NAMED 'WESLOSU'**

(50) Latin Name: *Lobelia erinus*
Varietal Denomination: Weslosu

(75) Inventor: Heinrich Westhoff, Südlohn (DE)

(73) Assignee: Gartenbau und Spezialkultwen Westhoff GbR, Südlohn (DE)

( * ) Notice: Subject to any disclaimer, the term of this patent is extended or adjusted under 35 U.S.C. 154(b) by 0 days.

(21) Appl. No.: 12/798,727

(22) Filed: Apr. 10, 2010

(51) Int. Cl.
*A01H 5/00* (2006.01)

(52) U.S. Cl. ..... Plt./451
(58) Field of Classification Search ..... Plt./451
See application file for complete search history.

*Primary Examiner* — June Hwu
*Assistant Examiner* — Louanne C Krawczewicz Myers
(74) *Attorney, Agent, or Firm* — C. A. Whealy

(57) ABSTRACT

A new and distinct cultivar of *Lobelia* plant named 'Weslosu', characterized by its compact, spherical, mounding and semi-trailing plant habit; vigorous growth habit; freely branching habit and short internodes; dense and bushy plant form; leaves covered with dense pubescence; continuously and freely flowering habit; violet blue-colored flowers with large white-colored centers; and relative tolerance to high temperatures.

2 Drawing Sheets

Botanical designation: *Lobelia erinus*.
Cultivar denomination: 'WESLOSU'.

BACKGROUND OF THE INVENTION

The present invention relates to a new and distinct cultivar of *Lobelia* plant, botanically known as *Lobelia erinus* and hereinafter referred to by the name 'Weslosu'.

The new *Lobelia* plant is a product of a planned breeding program conducted by the Inventor in Südlohn, Germany. The objective of the breeding program is to create new *Lobelia* plants with good vigor, uniform plant habit and attractive flower coloration.

The new *Lobelia* plant originated from a cross-pollination made by the Inventor in July, 2007 of a proprietary seedling selection of *Lobelia erinus* identified as code number 07P512, not patented, as the female, or seed, parent with *Lobelia erinus* 'Wesloti', disclosed in U.S. Plant Pat. No. 20,768, as the male, or pollen, parent. The new *Lobelia* was discovered and selected by the Inventor as a single flowering plant with the progeny of the stated cross-pollination grown in a controlled greenhouse environment in Südlohn, Germany in June, 2008.

Asexual reproduction of the *Lobelia* plant by vegetative cuttings in Südlohn, Germany since 2008, has shown that the unique features of this new *Lobelia* plant are stable and reproduced true to type in successive generations.

SUMMARY OF THE INVENTION

Plants of the new *Lobelia* have not been observed under all possible environmental conditions. The phenotype may vary somewhat with variations in environment such as temperature and light intensity without, however, any variance in genotype.

The following traits have been repeatedly observed and are determined to be the unique characteristics of 'Weslosu'. These characteristics in combination distinguish 'Weslosu' as a new and distinct cultivar of *Lobelia* plant:

1. Compact, spherical, mounding and semi-trailing plant habit.
2. Vigorous growth habit.
3. Freely branching habit and short internodes; dense and bushy plant form.
4. Leaves covered with dense pubescence.
5. Continuously and freely flowering habit.
6. Violet blue-colored flowers with large white-colored centers.
7. Relatively high temperature tolerant.

Plants of the new *Lobelia* differ from plants of the female parent selection in the following characteristics:

1. Plants of the new *Lobelia* have thicker and stronger lateral branches than plants of the female parent selection.
2. Stems and leaves of plants of the new *Lobelia* are pubescent whereas stems and leaves of plants of the female parent selection are glabrous.
3. Plants of the new *Lobelia* and the female parent selection differ in flower color.
4. Plants of the new *Lobelia* have smaller sepals than plants of the female parent selection.

Plants of the new *Lobelia* differ from plants of the male parent, 'Wesloti', in the following characteristics:

1. Plants of the new *Lobelia* are more compact than plants of 'Wesloti'.
2. Plants of the new *Lobelia* had thicker lateral branches than plants of 'Wesloti'.
3. Leaves of plants of the new *Lobelia* are ovate in shape whereas leaves of plants of 'Wesloti' are oblanceolate in shape.
4. Plants of the new *Lobelia* and 'Wesloti' differ in flower color as plants of 'Wesloti' have smaller white-colored centers than plants of the new *Lobelia*.
5. Plants of the new *Lobelia* have shorter peduncles than plants of 'Wesloti'.

Plants of the new *Lobelia* can be compared to plants of *Lobelia erinus* 'Wesloarc', disclosed in U.S. Plant Pat. No. 15,871. In side-by-side comparisons conducted in Südlohn, Germany, plants of the new *Lobelia* differed from plants of 'Wesloarc' in the following characteristics:

1. Plants of the new *Lobelia* were more compact than plants of 'Wesloarc'.
2. Plants of the new *Lobelia* were more trailing than and not as upright as plants of 'Wesloarc'.
3. Leaves of plants of the new *Lobelia* were less pubescent than leaves of plants of 'Wesloarc'.
4. Plants of the new *Lobelia* and 'Wesloarc' differed in flower color as plants of 'Wesloarc' had smaller white-colored centers than plants of the new *Lobelia*.
5. Plants of the new *Lobelia* had shorter peduncles than plants of 'Wesloarc'.

BRIEF DESCRIPTION OF THE PHOTOGRAPHS

The accompanying colored photographs illustrate the overall appearance of the new *Lobelia* plant, showing the colors as true as it is reasonably possible to obtain in colored reproductions of this type. Colors in the photographs may differ slightly from the color values cited in the detailed botanical description which accurately describe the actual colors of the new *Lobelia* plant.

The photograph on the first sheet comprises a side perspective view of a typical flowering plant of 'Weslosu' grown in a container.

The photograph at the top of the second sheet is a close-up view of a typical flowering plant of 'Weslosu'.

The photograph at the bottom of the second sheet is a close-up view of typical flowers and leaves of 'Weslosu'.

DETAILED BOTANICAL DESCRIPTION

Plants used for the aforementioned photographs and following description were grown under conditions which closely approximate commercial production conditions during the spring in 12-cm containers in a glass-covered greenhouse in Südlohn, Germany. During the production of the plants, day temperatures ranged from 20° C. to 25° C., night temperatures ranged from 16° C. to 18° C. and light levels ranged from 3,000 lux to 50,000 lux. Plants were pinched about two weeks after planting and were 27 weeks old when the photographs were taken and were 30 weeks old when the description was taken. In the following description, color references are made to The Royal Horticultural Society Colour Chart, 2001 Edition, except where general terms of ordinary dictionary significance are used.

Botanical classification: *Lobelia erinus* 'Weslosu'.

Parentage:

*Female parent.*—Proprietary seedling selection of *Lobelia erinus* identified as code number 07P512, not patented.

*Male parent.*—*Lobelia erinus* 'Wesloti', disclosed in U.S. Plant Pat. No. 20,768.

Propagation:

*Type cutting.*—Vegetative cuttings.

*Time to initiate roots, summer.*—About 10 to 14 days at 20° C.

*Time to initiate roots, winter.*—About 16 to 18 days at 20° C.

*Time to produce a rooted young plant, summer.*—About 21 to 24 days at 20° C.

*Time to produce a rooted young plant, winter.*—About 24 to 26 days at 20° C.

*Root description.*—Fine, fibrous; color, close to 158B.

*Rooting habit.*—Freely branching; moderately dense to dense.

Plant description:

*Plant form and growth habit.*—Compact, spherical, mounding and semi-trailing plant habit.; freely branching habit with lateral branches developing at potentially every node; short internodes; dense and bushy plant habit; vigorous growth habit.

*Plant height.*—About 8 cm to 10 cm.

*Plant width.*—About 32 cm to 40 cm.

*Main branch description.*—Diameter: About 2.5 mm. Internode length: About 1.3 cm. Strength: Strong, flexible. Texture: Densely pubescent. Color: Close to 146A to 146B.

*Lateral branch description.*—Length: About 12 cm to 22 cm. Diameter: About 1.7 mm. Internode length: About 1.2 cm. Strength: Strong, flexible. Texture: Densely pubescent. Color: Close to 146A to 146B.

Foliage description:

*Arrangement.*—Alternate, simple; sessile.

*Length, basal leaves.*—About 2.1 cm.

*Width, basal leaves.*—About 2.1 cm.

*Length, mid-plant leaves.*—About 3.6 cm.

*Width, mid-plant leaves: About* 2.3 cm.

*Length, apical leaves.*—About 2 cm.

*Width, apical leaves.*—About 8 mm.

*Shape, basal and mid-plant leaves.*—Ovate.

*Shape, apical leaves.*—Lanceolate.

*Apex, basal and mid-plant leaves.*—Cuspidate.

*Apex, apical leaves.*—Obtuse.

*Base, all leaves.*—Attenuate.

*Margin, basal and mid-plant leaves.*—Slightly crenate.

*Margin, apical leaves.*—Entire.

*Texture, all leaves, upper and lower surfaces.*—Densely pubescent; slightly rugose.

*Venation pattern, all leaves.*—Pinnate; arcuate.

*Color, all leaves.*—Developing leaves, upper surface: Close to 146A. Developing leaves, lower surface: Close to 146B. Fully expanded leaves, upper surface: Close to 147A; venation, slightly lighter than 147A. Fully expanded leaves, lower surface: Close to 147B; venation, slightly lighter than 147B.

Flower description:

*Flower arrangement, habit and shape.*—Flowers typically arranged in racemes; flowers held mostly outwardly; freely and continuously flowering; older flowers are overgrown by new flowers and leaves; freely flowering habit with typically about seven to nine flowers per lateral branch; flowers tubular with three larger lower petals and two smaller upper petals.

*Fragrance.*—None detected.

*Natural flowering season.*—April until frost in Germany; plants begin flowering about 14 weeks after planting.

*Flower longevity on the plant.*—Longevity of individual flowers is highly dependent on weather conditions, flowers typically last about one week on the plant; flowers not persistent.

*Inflorescence height.*—About 9 cm to 12 cm.

*Inflorescence diameter.*—About 7 cm.

*Flower diameter.*—About 1.9 cm.

*Flower depth (height).*—About 1.8 cm.

*Flower throat diameter.*—About 4 mm.

*Flower tube length.*—About 7 mm.

*Flower tube diameter, at the base.*—About 2.5 mm.

*Flower buds, developing.*—Length: About 1 cm. Diameter: About 5 mm. Shape: Oblong. Color: Towards the base, close to 145C; mid-section, close to 145B; towards the apex, close to 145A.

*Petals.*—Arrangement: Single whorl of five petals, fused; three larger lower petals and two smaller upper petals. Three lower petals: Length, above throat: About 1 cm. Width: About 8 mm. Shape: Obovate. Apex: Slightly cuspidate. Margin: Entire. Texture, upper and lower surfaces: Smooth, glabrous. Two upper petals: Length, above throat: About 6 mm. Width: About 2.5 mm Shape: Oblanceolate. Apex: Slightly cuspidate. Margin: Entire. Texture, upper and lower surfaces: Smooth, glabrous. Color, upper petals: When opening, upper surface: Close to 95A to 95B. When opening, lower surface: Close to 97A. Fully opened, upper surface: Close to 95A to 95C; venation color similar to surface color: color becoming closer to 96B with development. Fully opened, lower surface: Between 96C and 97C; venation color similar to surface color; color becoming closer to 97B with development. Color, lower petals: When opening, upper surface: Towards the apex, close to 95A to 95B; mid-section and base, close to 155D. When opening, lower surface: Close to 97A; towards the base, close to 155D. Fully opened, upper surface: Towards the apex, close to 95A to 95C; mid-section and base, close to 155D; venation color similar to surface color: color becoming closer to 96B with development. Fully opened, lower surface: Between 96C and 97C; towards the base, close to 155D; venation color similar to surface color; color becoming closer to 97B with development. Throat: Close to 97D; venation, close to 96A. Tube: Close to 92D and 97B.

*Sepals.*—Arrangement: Single whorl of five sepals, fused at the base; star-shaped calyx. Length: About 8 mm. Width: About 1.7 mm. Shape: Narrowly deltoid. Apex: Acute. Margin: Entire. Texture, upper and lower surfaces: Pubescent. Color, upper surface: Close to 147A. Color, lower surface: Close to 147B.

*Peduncles.*—Length: About 6 cm to 10 cm. Diameter: About 1.5 mm to 2 mm. Strength: Strong, flexible. Texture: Pubescent. Color: Close to 137B.

*Pedicels.*—Length: About 1.2 cm to 1.8 cm. Diameter: About 0.9 mm. Strength: Strong, flexible; wiry. Texture: Pubescent. Color: Close to 137B.

*Reproductive organs.*—Stamens: Quantity per flower: About five. Filament length: About 3 mm to 4 mm. Filament color: Close to 155C. Anther length: About 2.2 mm. Anther width: About 2.1 mm. Anther color: Close to N186A to N186B. Pollen amount: Moderate. Pollen color: Close to 9C. Pistils: Quantity per flower: One. Pistil length: About 9 mm. Stigma shape: Ovate, two-parted. Stigma color, immature: Close to 83A. Stigma color, mature: Close to 83D. Style length: About 5 mm. Style color: Close to 145B to 145C. Ovary color: Close to 144A.

*Fruits/seeds.*—Fruit and seed development have not been observed on plants of the new *Lobelia.*

Disease/pest resistance: Plants of the new *Lobelia* have not been noted to be resistant to pathogens and pests common to *Lobelia.*

Temperature tolerance: Plants of the new *Lobelia* have been observed to tolerate temperatures from about 6° C. to 8° C. about 30° C. to 32° C.

It is claimed:

1. A new and distinct *Lobelia* plant named 'Weslosu' as illustrated and described.

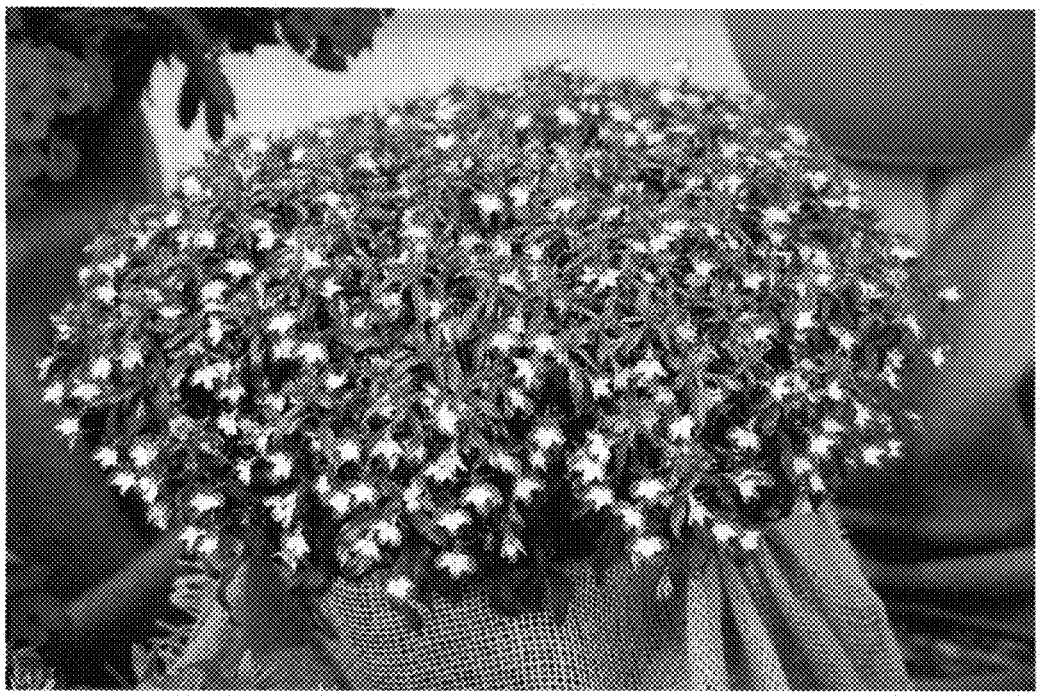

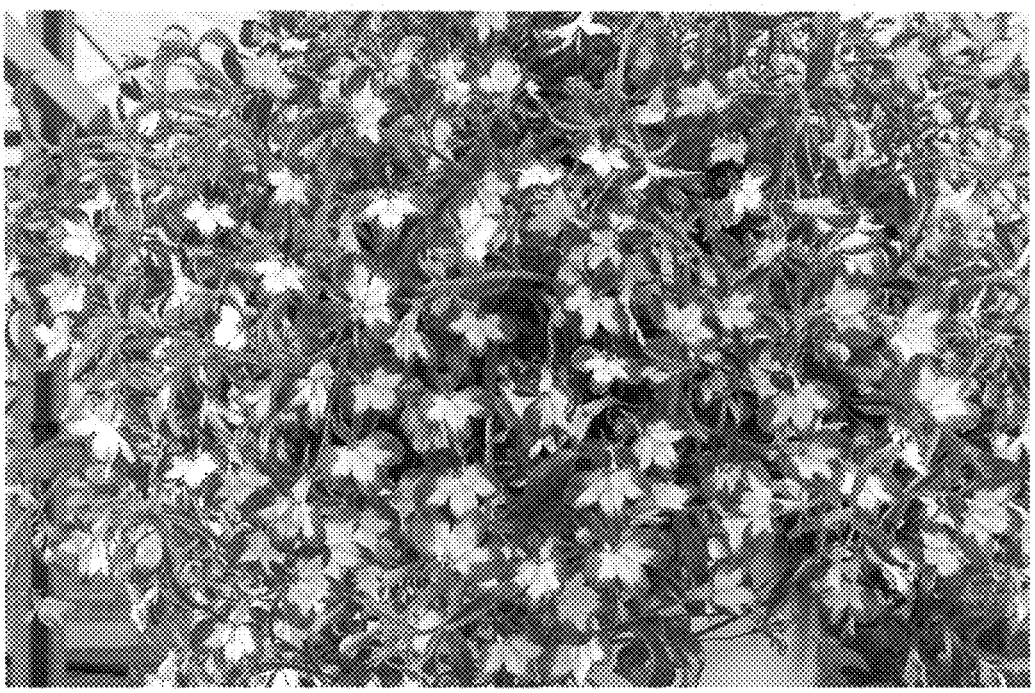
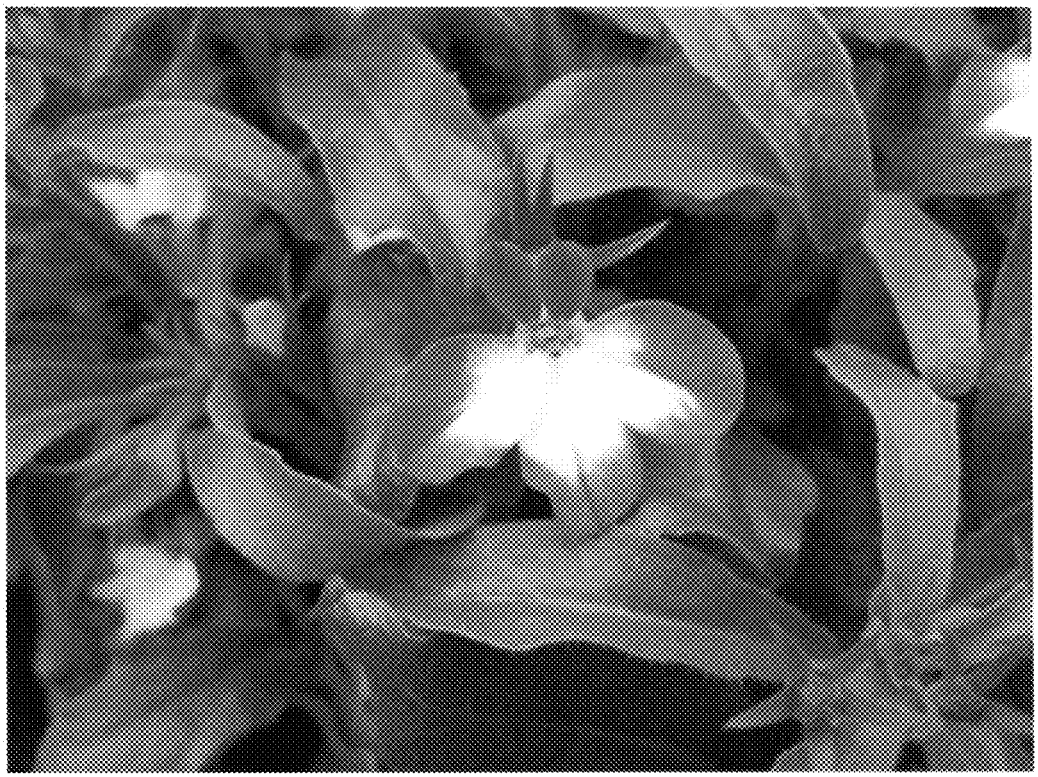

* * * * *